United States Patent [19]

Radel et al.

[11] 4,379,939

[45] Apr. 12, 1983

[54] PREPARATION OF NITROGEN FERTILIZERS FROM OXALATE ESTERS PREPARED BY THE OXIDATIVE CARBONYLATION OF ALCOHOLS OVER NOBLE METAL CATALYSTS UTILIZING REGENERABLE 2,5-CYCLOHEXADIENE-1,4-DIONE OXIDANTS

[75] Inventors: Robert J. Radel; Jack M. Sullivan, both of Florence, Ala.

[73] Assignee: Tennessee Valley Authority, Muscle Shoals, Ala.

[21] Appl. No.: 164,418

[22] Filed: Jun. 30, 1980

Related U.S. Application Data

[63] Continuation of Ser. No. 137,204, Apr. 4, 1980, now Defensive Publication No. T100,903.

[51] Int. Cl.$^3$ .................... C07C 69/36; C07C 67/36
[52] U.S. Cl. .................... 560/193; 260/396 R; 560/204; 564/135; 564/136; 568/753; 568/772
[58] Field of Search .................... 560/204, 193; 260/396 R; 564/135; 568/753, 772

[56] References Cited

U.S. PATENT DOCUMENTS

| | | | |
|---|---|---|---|
| 3,393,136 | 7/1968 | Fenton et al. | 560/204 X |
| 3,992,436 | 11/1976 | Zehner | 560/204 |
| 3,994,960 | 11/1976 | Yamazaki et al. | 560/204 |
| 4,005,128 | 1/1977 | Zehner et al. | 560/204 |
| 4,005,129 | 1/1977 | Zehner | 560/204 |
| 4,005,130 | 1/1977 | Zehner | 560/204 |
| 4,005,131 | 1/1977 | Zehner | 560/204 |
| 4,041,067 | 8/1977 | Zehner et al. | 560/204 X |
| 4,065,490 | 12/1977 | Zehner | 560/204 |
| 4,069,388 | 1/1978 | Zehner | 560/204 |
| 4,118,589 | 10/1978 | Cassar et al. | 560/204 |
| 4,160,107 | 7/1979 | Agnes et al. | 560/204 |

FOREIGN PATENT DOCUMENTS 2514685 10/1975 Fed. Rep. of Germany.

OTHER PUBLICATIONS

Fenton et al. II, J. Org. Chem., vol. 39, No. 5, pp. 701–704, (1974).

*Primary Examiner*—Natalie Trousof
*Assistant Examiner*—Vera C. Clarke
*Attorney, Agent, or Firm*—Robert A. Petrusek

[57] ABSTRACT

A process for the preparation of nitrogen fertilizers, especially oxamide, either indirectly, or directly from oxalate esters, including the regeneration of the quinone oxidant utilized in the formation of the above esters.

Preparation of oxalate esters as potential intermediates for nitrogen fertilizers by the oxidative carbonylation of alcohols with carbon monoxide in the presence of a catalytic amount of a platinum group metal salt with or without a corresponding metal oxidant salt and an optionally substituted quinone (substituted or unsubstituted 2,5-cyclohexadiene-1,4-dione). High yields of isolated dialkyl oxalates are obtained by regulating temperature and carbon monoxide pressure and by maintaining essentially anhydrous conditions. In addition, high yields of the hydroquinones (1,4-dihydroxybenzenes) are recovered.

20 Claims, No Drawings

PREPARATION OF NITROGEN FERTILIZERS FROM OXALATE ESTERS PREPARED BY THE OXIDATIVE CARBONYLATION OF ALCOHOLS OVER NOBLE METAL CATALYSTS UTILIZING REGENERABLE 2,5-CYCLOHEXADIENE-1,4-DIONE OXIDANTS

The invention herein described may be manufactured and used by or for the Government for governmental purposes without the payment to us of any royalty therefor.

This is a continuation of our copending application Ser. No. 137,204, filed Apr. 4, 1980, for PREPARATION OF NITROGEN FERTILIZERS FROM OXALATE ESTERS PREPARED BY THE OXIDATIVE CARBONYLATION OF ALCOHOLS OVER NOBLE METAL CATALYSTS UTILIZING REGENERABLE 2,5-CYCLOHEXADIENE-1,4-DIONE OXIDANTS, now U.S. Defensive Publication No. T100903.

The present invention relates to: (1) a process for the production of nitrogen fertilizers, particularly oxamide, from intermediate oxalate esters; (2) a process for the production of said intermediate oxalate esters by the oxidative carbonylation of alcohols over platinum group metal catalysts with or without corresponding metal oxidant salts; and (3) utilizing quinones (2,5-cyclohexadiene-1,4-diones) as regenerable oxidant feedstock to said processes (1) and (2), supra.

Oxamide produced according to the present invention has its chief use as an agricultural product due to its favorable slow-release fertilizer characteristics. Oxalate esters produced according to the present invention have many important commercial applications including their use as metal polishing agents, solvents for cellulose ether or ester resins, in the production of pharmaceuticals and glycols and as intermediates in the production of dyes, agricultural products, and fertilizers. Fertilizer and agricultural products which can be manufactured from these esters include such products as oxamide, oxalyl diureide, parabanic acid, allantoin, etc., as slow-release fertilizers or urease and nitrification inhibitors. The hydroquinones (1,4-dihydroxybenzenes) and 2,5-cyclohexadiene-1,4-diones of the present invention also have many important commercial applications. The 2,5-cyclohexadiene-1,4-diones can be used as oxidants in the oxidative carbonylation reaction, as oxidants in the preparation of vinylic fatty acid esters, and as feedstocks for other industrially and pharmaceutically important chemicals. The 1,4-dihydroxybenzenes also have wide application in the photographic industry.

BACKGROUND OF THE INVENTION

Embodiment No. 1

A number of prior-art processes have been described for the preparation of oxalate esters by the oxidative carbonylation of alcohols with carbon monoxide. These prior-art processes generally involve the use of oxygen or oxygen-containing gases, noble metal salt catalysts, and metal oxidant salts as well as dehydrating agents or azeotropic distillations to eliminate the presence of water.

The present invention describes an improved process for the oxidative carbonylation of alcohols in which an alcohol is reacted with carbon monoxide in the presence of a noble metal salt catalyst with or without the corresponding metal oxidant salt and with a substituted or unsubstituted 2,5-cyclohexadiene-1,4-dione as oxidant at suitable temperatures and pressures. The 1,4-dihydroxybenzene formed from the above reaction may be reoxidized by the process described in Embodiment No. 3, infra, to provide a cyclic process or may themselves be purified for sale as a valuable industrial chemical.

U.S. Pat. No. 3,393,136 describes a process in which carbon monoxide is oxidized in the presence of a platinum group metal catalyst, a ferric or cupric metal oxidant salt, and a water scavenger such as orthoformate ester. The salts are returned to their oxidized states through the introduction of oxygen or oxygen-containing gases or by application of a direct current electrical potential to the reaction zone. When oxygen is employed, explosive mixtures of organic vapors in the gas phase must be avoided.

A West German Pat. No. 2,213,435 describes a method for the synthesis of oxalic acid and oxalate esters. Water or alcohol is reacted with carbon monoxide and oxygen in the presence of a platinum group metal salt, the salt of a metal more electropositive than platinum, and an alkali metal salt. A disadvantage of this reaction is that explosive mixtures of oxygen and carbon monoxide are necessary to effect the reaction.

A series of patents (U.S. Pat. No. 3,994,960; German Offen. No. 2,514,685; Japan Kokai 77 31,015, 76 29,424, 76 95,031 and 76 105,008) have been issued to T. Yamasaki and coworkers, disclosing a process for the preparation of dialkyl oxalates utilizing carbon monoxide and oxygen. Carbon monoxide, alcohol, and small increments of oxygen are reacted in the presence of a platinum group metal salt, a salt of copper or iron, and an accelerator composed of one or more components. The use of promoters is said to decrease the necessity for maintaining anhydrous conditions. With the use of oxygen, however, explosive mixtures may still be formed.

L. R. Zehner has also been issued a series of patents (U.S. Pat. Nos. 4,005,128-131; 4,041,067-8; 4,065,490; 4,069,388; 3,992,436; German Offen. Nos. 2,721,734 and 2,808,574) describing similar processes. These processes involve the reaction of carbon monoxide, alcohols, or other alcohol sources and oxygen or oxygen-containing gases in the presence of a platinum group metal salt or complex, a metal oxidant salt, and an amine base or the salt of an amine base. Again, the use of oxygen permits the possible formation of explosive mixtures.

D. M. Fenton and P. J. Steinwand (J. Org. Chem. 39 (5), 701–4, 1974) have described the synthesis of oxalate esters by the reaction of carbon monoxide and alcohol in the presence of a palladium (II) chloride-copper (II) chloride redox couple, oxygen, and dehydrating agents. The use of benzoquinone as an oxidant and palladium (II) chloride catalyst with or without dehydrating agents is shown. In the absence of dehydrating agents and at low carbon monoxide pressure and long reaction times, only low yields of oxalate (2.4 percent) and carbonate (2.8 percent) were obtained.

U.S. Pat. No. 4,005,130 discloses a process for the production of oxalate esters by the oxidative carbonylation of alcohols with carbon monoxide in the presence of a catalytic amount of copper, nickel, cadmium, cobalt, or zinc metal salt catalyst and a substituted or unsubstituted 2,5-cyclohexadiene-1,4-dione. Yields of oxalate esters approach 50 percent while oxalate to carbonate ratios of 2 to 4 were common. Yields were based on gas-liquid phase chromatography and do not reflect isolated esters.

The oxalate products of the present invention have many important commercial applications including their use as solvents for cellulose ether or ester resins, in the preparation of pharmaceuticals and glycols, and as intermediates in the production of dyes, agricultural products, and a number of potential slow-release fertilizers, a known example of which is oxamide.

Advantages of the present invention over the prior-art processes are: (1) the high conversion and selectivity toward oxalate esters over the competing carbonate esters, (2) the increased rate of reaction thus reducing the time necessary to effect the reaction, (3) elimination of the hazardous operational conditions by avoiding hazardous mixtures of oxygen and carbon monoxide, (4) avoiding the necessity of employing dehydrating agents to remove water, and (5) the recovery of the 1,4-dihydroxybenzene formed in the reaction in nearly quantitative yield for its subsequent regeneration or purification for sale as a valuable industrial chemical.

Embodiment No. 2

A number of prior-art processes have been described for the preparation of oxamide. Conventional procedures involve the processing of oxalic acid which may be prepared by dehydrogenation of alkali formates. Other prior-art processes generally proceed through intermediates such as cyanogen and hydrogen cyanide, two very toxic and extremely hazardous chemicals. Another prior-art process describes the conversion of oxalate esters to oxamide in nearly quantitative yield. However, the oxalate esters are prepared by processes involving the use of alcohols, carbon monoxide, and oxygen or oxygen-containing gases, noble metal salt catalysts, and metal oxidant salts as well as dehydrating agents or azeotropic distillations to eliminate water.

This embodiment of the present invention describes an improved process for the preparation of oxamide via the oxidative carbonylation of alcohols in which an alcohol is reacted with carbon monoxide in the presence of a noble metal salt catalyst and with an optionally substituted 2,5-cyclohexadiene-1,4-dione at suitable temperatures and pressures (as described in Embodiment 1 of this invention). The catalyst is then filtered for recycle and the resulting solution ammoniated at low temperatures to provide oxamide. The 1,4-dihydroxybenzene produced in the reaction may be reoxidized by known methods to provide a cyclic process or may itself be purified for sale as a valuable industrial chemical. The alcohol formed during ammoniation of the oxalate esters is also recycled.

T. Yamashita and coworkers (Japan Kokai 76 29,430 Mar. 12, 1976) describe a process for the preparation of oxamide by the reaction of hydrogen cyanide with nitric acid in aqueous solution containing copper (II) ion. A 99-percent conversion of HCN was reported, giving a 77 percent yield of oxamide. Effluent gases containing 1 percent or more hydrogen cyanide, a very toxic material, must be scrubbed or further dealt with.

Hydrogen cyanide has also been used to prepare cyanogen which can then be converted to oxamide. The most promising of these methods has been developed by W. Riemenschneider (British Pat. No. 1,148,871). The one-step process involves contacting hydrogen cyanide and oxygen with an aqueous acetic acid solution of cupric nitrate at atmospheric pressure and temperatures of 50° C. to 80° C. Although the conversion is high, small amounts of hydrogen cyanide and cyanogen remain in the effluent gases.

In addition to its toxic and hazardous characteristics, the erratic availability of hydrogen cyanide to the world market is also a disadvantage to these processes.

T. Yamasaki of Ube Industries, Ltd., has reported a process (Japan Kokai 77 07,916, Jan. 21, 1977) for the preparation of oxamide from oxalic diesters. The reaction is carried out by dissolving the ester in an aliphatic alcohol at a concentration given by $T \geq (1.07 \times 10^{-2})C^2 + (4.65 \times 10^{-1})$ C-13.5, where T is the reaction temperature (20 C.) and C is the concentration of ester in weight percent, and treating with ammonia. Quantitative yields of oxamide are produced. The oxalate esters used were obtained via the oxidative carbonylation of alcohols, utilizing oxygen as the oxidizing agent.

Advantages of the present invention over the prior-art processes are: (1) the relative innocuous characteristics of oxalate esters as intermediates in the production of oxamide, (2) the high conversion and selectivity toward oxalate esters over the competing carbonate esters, (3) the quantitative yields of oxamide produced without isolation of the oxalate esters, (4) the elimination of hazardous operating conditions by the avoidance of explosive mixtures of carbon monoxide and oxygen, (5) the recovery of the 1,4-dihydroxybenzenes formed in the reaction in nearly quantitative yield for its subsequent recycle or purification for sale as a valuable industrial chemical, and (6) recycle of the alcohols.

Embodiment No. 3

A number of prior-art processes have been proposed for the preparation of 2,5-cyclohexadiene-1,4-diones or quinhydrones from 1,4-dihydroxybenzenes. Such prior-art processes encompass the use of expensive, corrosive and in some cases toxic inorganic oxidizing agents or the use of precious metal catalysts in acid media, or other high-boiling solvents which hinder the subsequent isolation of quinone.

This embodiment of the present invention discloses an improved process for the oxidation of 1,4-dihydroxybenzenes (hydroquiones) to 2,5-cyclohexadiene-1,4-diones (quinones) or the corresponding quinhydrones (a 1:1 molecular complex of 1,4-dihydroxybenzene and 2,5-cyclohexadiene-1,4-dione) with specific metal salt catalysts and oxygen or air in a suitable solvent and at suitable temperature and pressure conditions.

A French Pat. No. 1,388,869 obtained by Rhone-Poulene discloses a procedure for the regeneration of 2,5-cyclohexadiene-1,4-dione from 1,4-dihydroxybenzene in acetic acid solution by contacting the above solution with oxygen-containing gases in the presence of a catalyst consisting of ruthenium or rhodium on an inert support.

The disadvantages of such a process arise if the regenerated quinone (i.e., 2,5-cyclohexadiene-1,4-dione) is to be isolated or if it is to be further utilized in some process requiring a nonacidic, anhydrous media, as significant losses result from the attempted separation of 2,5-cyclohexadiene-1,4-dione from the acetic acid solution. Also, in order to maintain a high catalytic activity, it is necessary to treat the catalyst with hydrogen between each oxidation, thus adding additional costly steps to the process.

Michel Vignau in a recent West German Pat. No. 2,231,677, discloses a process for the conversion of compounds containing a hydroxyl group bonded to a carbon atom, to the corresponding carbonyl compound, in nonprotic solvents, using silver silicate as the oxidizing agent. Thus, the 1,4-dihydroxybenzene, silver silicate, and the organic solvent are brought into contact, refluxed for a period of time after which the silver silicate is removed by filtration and the liquid fraction containing the 2,5-cyclohexadiene-1,4-dione is further purified. The disadvantages of this process lie in the use of a fivefold excess of expensive siler silicate and the difficulty of regenerating the active oxidizing agent.

Early studies of the autoxidation of unsubstituted hydroquinones have shown the coproduction of hydrogen peroxide to cause complicated side reactions involving nuclear hydrogens [T. H. James, J. M. Snell, and A. Weissberger, *J. Amer. Chem. Soc.* 60, 2084 (1938)]. These side reactions have generally been responsible for the low yields of quinones when oxygen is used as the oxidizing agent, with or without a catalyst. These side reactions are also implicated in several recent attempts to perform the autoxidation of 1,4-dihydroxybenzenes in the presence of a dioxygen complex [A. McKillop and L. J. Ray, *Synthesis*, 1977 (12), 847], in the presence of an electrochemically generated cobalt phthalocyanine complex [S. Meshitsuka, M. Ichikawa and K. Tamarce, *J. Chem. Soc., Chem. Commun.*, 1975 (9), 360-1], and in the presence of a zinc oxide catalyst in weak acid media [K. Hauffe and H. Pusch, Ber. Bunsenges, *Phys. Chem.* 72 (6), 669 (1968)].

The advantages of this embodiment of the present invention, as compared to prior-art processes, are (1) high conversions and high selectivity to the quinone or quinhydrone over the polymeric material; (2) catalysis of the oxidative regeneration with relatively inexpensive metal salt catalysts such as copper (I) chloride; (3) elimination of the necessity for the presence of water-miscible acids; and (4) greater ease in the isolation of the product quinone from the reaction mixture, with a resulting increase in isolated yield.

SUMMARY OF THE INVENTION

Embodiment No. 1 of the present invention provides a greatly improved process for the oxidative carbonylation of alcohols to produce high yields of alkyl oxalates. The process is carried out by reacting carbon monoxide with an alcohol at elevated temperatures and pressures in the presence of a platinum group metal salt with or without the corresponding metal oxidant salt and a substituted or unsubstituted 2,5-cyclohexadiene-1,4-dione under essentially anhydrous conditions.

It has been found that the above reaction can be carried out with high conversion and with high selectivity toward the oxalate ester over the carbonate ester. The reaction is carried out in the presence of palladium salts, such as the palladium (II) halides, with or without solvents, such as acetonitrile, and with a substituted or unsubstituted 2,5-cyclohexadiene-1,4-dione as an oxidant. In addition, a metal oxidant salt may also be employed in the reaction.

It is the primary object of Embodiment No. 1 of this invention to provide an improved and economical process for the preparation of oxalate esters in high yield while avoiding the operational difficulties associated with the prior-art processes.

It is also an object of Embodiment No. 1 of this invention to provide a process in which the 1,4-dihydroxybenzenes obtained during the reaction may be utilized in a cyclic manner or further purified for sale by concurrently maximizing their yields and purity.

It is a further object of Embodiment No. 1 of this invention to provide an improved method for the preparation of commercially important dimethyl oxalate in high yield and of purity sufficient to be used in the further production of oxamide.

It is a further object of Embodiment No. 1 of this invention to minimize side reactions of the 2,5-cyclohexadiene-1,4-diones and 1,4-dihydroxybenzenes present in the reaction medium so as to effect their maximum recovery.

Embodiment No. 2 of the present invention provides an improved process for the production of oxamide via the oxadative carbonylation of alcohols. The process is carried out by reacting carbon monoxide with an alcohol at elevated temperatures and pressures in the presence of a platinum group metal salt catalyst and an optionally substituted 2,5-cyclohexadiene-1,4-dione under essentially anhydrous conditions. This solution is then filtered to remove the catalyst and ammoniated at low temperatures to precipitate oxamide. The 1,4-dihydroxybenzene formed is either purified for sale or recycled along with the alcohol and catalyst.

It has been found that the above reactions can be carried out with high conversion and selectivity toward oxalate esters and thus also to oxamide. The oxidative carbonylation is carried out in the presence of palladium (II) salts, such as palladium (II) chloride, with or without co-solvents, such as acetonitrile.

It is the primary object of Embodiment No. 2 of this invention to provide an improved and economical process for the production of oxamide in high yield while avoiding the operational difficulties and hazardous materials associated with the prior-art processes.

It is also the object of Embodiment No. 2 of this invention to provide a process in which the 1,4-dihydroxybenzenes obtained during the reaction may be utilized in a cyclic manner or further purified for sale by concurrently maximizing their yield and purity.

Embodiment No. 3 of the present invention describes a much improved process for the oxidative regeneration of 2,5-cyclohexadiene-1,4-diones and quinhydrones from 1,4-dihydroxybenzenes by reacting them with oxygen in the presence of a copper salt catalyst or with ruthenium or rhodium metal catalysts deposited on an inert support in nitrile or nitrile-containing solvent systems.

It has been found that the above-mentioned oxidative regeneration may be carried out on substituted or unsubstituted hydroquinones. The oxidative regeneration of the substituted derivatives may also be carried out in alcohol solvents, as well as in nitrile or nitrile-containing solvents.

It is a primary object of Embodiment No. 3 of this invention to provide an improved and economical process for the oxidative regeneration of 2,5-cyclohexadiene-1,4-diones and quinhydrones from 1,4-dihydroxybenzenes in high yields, while avoiding the side reactions and isolation problems associated with the prior-art processes.

It is another object of Embodiment No. 3 of this invention to provide a process compatible with the cyclic use of the 2,5-cyclohexadiene-1,4-diones and quinhydrones as oxidizing agents in the production of other commercially important chemicals.

It is a further object of Embodiment No. 3 of this invention to provide a specific process for the employment of a copper salt catalyst and oxygen in an oxidative regeneration of an aromatic-1,4-dihydroxy compound to the corresponding diketone.

A further object of Embodiment No. 3 of this invention is to provide an improved process for the preparation of the commercially important 2,5-cyclohexadiene-1,4-dione.

It is also the object of this invention to provide a process in which the alcohols may be recycled.

It is a further object of this invention to provide a process for the production of oxamide in which only carbon monoxide, ammonia, and oxygen are consumed.

These and other objects and advantages of the invention will become apparent from the description of the invention which follows and from the claims.

DESCRIPTION OF THE INVENTION

Oxalate esters are produced according to Embodiment No. 1 of this invention by reacting an alcohol with carbon monoxide under relatively anhydrous liquid phase conditions at elevated temperatures and pressures and in the presence of a substituted or unsubstituted 2,5-cyclohexadiene-1,4-dione and a platinum group metal salt with or without a corresponding metal oxidant salt. The synthesis is carried out according to equation 1 of the following depiction.

EQUATIONS FOR THE PRODUCTION OF OXALATE ESTERS, OXAMIDE AND THE REGENERATION OF 2,5-CYCLOHEXADIENE-1,4-DIONES

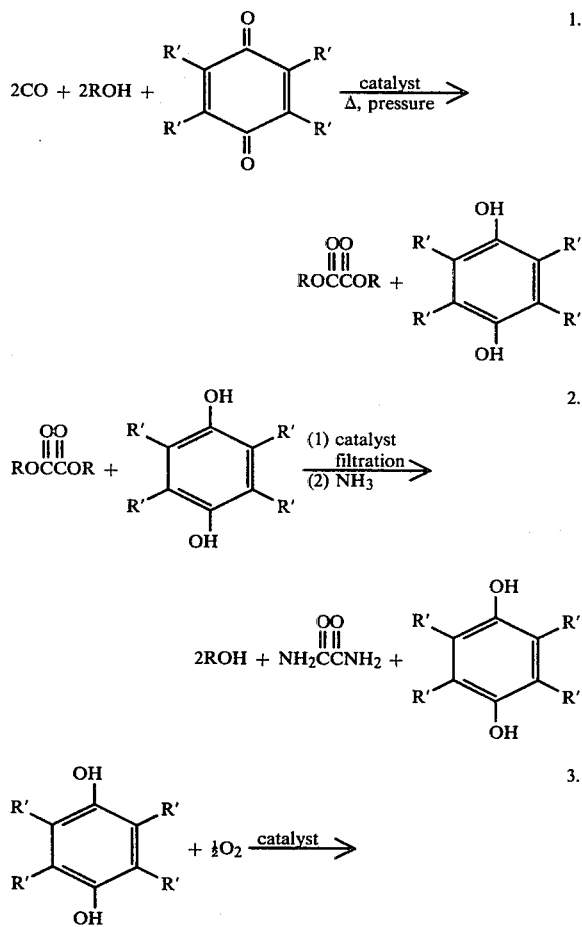

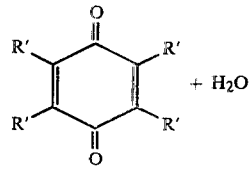

wherein R is selected from monohydric substituted or unsubstituted aliphatic, alicyclic, or aromatic groups and R' may be hydrogen, halogen, or aliphatic, alicyclic, or aromatic groups. The 2,5-cyclohexadiene-1,4-dione employed in the reaction functions as both an oxidant and as a hydrogen acceptor. The reaction may also be carried out in the presence of a solvent, in which case the alcohol must be present in at least stoichiometric amounts.

The reaction according to Embodiment No. 1 of this invention may be carried out in an autoclave or any other suitable well-stirred pressure reactor. The general procedure is to charge the alcohol, solvent if used, catalyst, and oxidant into the reaction vessel and to introduce the proper amount of carbon monoxide to obtain the desired reaction pressure while stirring, and heating to the desired temperature for the appropriate period. The reaction can also be carried out as a continuous process. The catalysts are recovered by filtration, the 1,4-dihydroxybenzenes and oxalates by crystallization and distillation.

The process takes place and is performed under relatively anhydrous liquid phase conditions. In general, the alcohols employed in the practice of this invention are monohydric saturated aliphatic and alicyclic alcohols or aromatic alcohols. The alcohols may contain other substituents such as halo, amido, cyano, alkoxy, and amino groups. These substituents generally do not interfere with the oxidative carbonylation. The alcohols may be used either alone or in the presence of a co-solvent. If such a co-solvent is used, the alcohol must be present in at least stoichiometric quantities with respect to the oxidant to achieve maximum yield.

Co-solvents which may be used in the reaction include, for example, organic esters and nitriles such as methyl, ethyl, isopropyl, and butyl acetates, acetonitrile, alkyl benzoates, etc., as well as other organic solvents nonreactive to carbon monoxide under the reaction conditions.

The alcohols utilized in the process of this invention may be primary, secondary, or tertiary alcohols conforming to the general formula ROH wherein R is any substituted or unsubstituted aliphatic, alicyclic, or aromatic alcohol, preferably containing 1 to 10 carbons. Representative alcohols especially suitable for use in this invention are methyl, ethyl, n-propyl, isopropyl-, n-, iso-, and sec-butyl, amyl, hexyl, octyl, lauryl, and benzyl alcohols. Alicyclic alcohols such as cyclohexanol, cyclooctanol, cycloheptanol, cyclodecanol, and cycloundecanol may also be employed.

The nitriles used as co-solvent in the process of this invention may be primary, secondary, or tertiary conforming to the general formula RCN wherein R is a substituted or unsubstituted aliphatic, alicyclic, or aromatic group containing 1 to 10 carbon atoms and which is a liquid at or above 30° C. Representative nitriles especially suitable for use in this invention are acetonitrile, ethanonitrile, propionitrile, butyronitrile, pentanonitrile, hexanonitrile, and heptanonitrile as well as benzo-, cyclohexyl-, cyclopentyl-, cycloheptyl-, and cyclooctylnitrile.

The oxidants which may be used in the process of this invention are the substituted or unsubstituted 2,5-cyclohexadiene-1,4-diones of the general formula

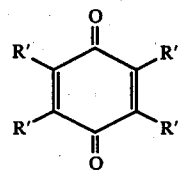

wherein R' is hydrogen, halogen, or alkyl group or part of an aromatic ring as in anthraquinone. In addition to 2,5-cyclohexadiene-1,4-dione itself, representative diones include the mono-, di-, tri-, and tetra-substituted chloro, bromo, iodo, and fluoro compounds as, for example, 2-chloro-, 2-bromo-, 2-fluoro-, and 2-iodo-2,5-cyclohexadiene-1,4-dione, 2,5-, 2,6-, and 2,3-dichloro-, dibromo-, difluoro-, and diiodo-2,5-cyclohexadiene-1,4-dione, 2,3,5-trichloro-, tribromo-, trifluoro-, and triiodo-2,5-cyclohexadiene-1,4-dione, and the 2,3,5,6-tetrachloro-, tetrabromo-, tetrafluoro-, and tetraiodo-2,5-chclohexadiene-1,4-diones. Representative alkyl-substituted 2,5-cyclohexadiene-1,4-diones are 2-methyl-, 2-ethyl-, and 2-propyl-2,5-chclohexadiene-1,4-diones, the 2,5-, 2,6-, and 2,3-dimethyl-, diethyl-, and dipropyl-2,5-cyclohexadiene-1,4-diones, the 2,3,5-trimethyl-, 2,3,5-triethyl-, and 2,3,5-tripropyl-2,5-cyclohexadiene-1,4-dione and the 2,3,5,6-tetramethyl- and tetraethyl-2,5-chclohexadiene-1,4-dione. In addition, such other diones may be employed as 2,3-dichloro-5,6-dicyano-2,5-cyclohexadiene-1,4-dione.

The catalysts employed in the process of this invention are the salts of the platinum group metals, palladium (II), platinum (II), rhodium (III), and ruthenium (III). Among the structures of the metal compounds which may be used are the palladium, platinum, rhodium, or ruthenium halides, oxalates, acetates, and sulfates. Representative platinum group metal salt catalysts include, for example, palladium (II) chloride, rhodium (III) chloride, palladium (II) sulfate, palladium (II) oxalate, palladium (II) acetate, palladium (II) iodide,, rhodium (III) bromide, platinum (II) chloride, and platinum (II) sulfate.

The catalyst may be employed in a homogeneous state in the reaction mixture at reaction conditions. The use of a ligand or coordination complex compound of the metal salt catalyst may be used to render the metal salts more soluble in the reaction medium. The ligands may be, for example, alkyl or arylphosphines, arsines, or stibines. The complexes which are suitable in the present invention include the complex compounds of palladium (II), platinum (II), rhodium (III), and ruthenium (III) and may contain one or more than one metal atom per molecule. With multimetal atom complexes the metals may be the same or different. The mono- or polydentate ligands present in the molecule must contain at least one electron-donating atom such as phosphorus, arsenic, or antimony and is generally an organophosphine, arsine, or stibine. Representative suitable monodentate ligands include, for example, alkyl phosphines such as triethyl-, trimethyl-, and tributyl phosphine; aryl phosphines such as triphenylphosphine; and mixed alkylarylphosphines such as diethylphenylphosphine. Phosphites such as triphenyl phosphite may also be employed. Representative polydentate ligands include, for example, tetramethyl diphosphinoethane and tetraphenyl diphosphinoethane. These complexes may be introduced into the reaction medium as such, or the may be formed in situ from the suitable metal or metals and ligands.

Oxamide is produced according to Embodiment No. 2 of this invention via the oxidative carbonylation of alcohols under relative anhydrous liquid phase conditions at elevated temperatures and pressures in the presence of an optionally substituted 2,5-chclohexadiene-1,4-dione and a platinum group metal salt as described in Embodiment No. 1. After catalyst filtration, the oxalate esters formed in situ are subjected to aminolysis at low temperatures to precipitate the oxamide. This embodiment is carried out according to equation 2 of the depiction, supra, wherein R is selected from monohydric substituted or unsubstituted aliphatic, alicyclic, or aromatic groups and R' may be hydrogen, halogen, aliphatic, or aromatic groups.

The oxidative carbonylation according to the invention may be carried out in an autoclave or any other suitable well-stirred pressure reactor. The general procedure is to charge the alcohol, co-solvent (if used), catalyst, and oxidant into the reaction vessel and introduce the proper amount of carbon monoxide while stirring to obtain the desired reaction pressure and heating to the desired temperature for the appropriate period. The reaction can also be carried out as a continuous process. The catalyst is recovered by filtration and the oxalate ester ammoniated in situ at low temperatures to precipitate oxamide and to regenerate the alcohol. The 1,4-dihydroxybenzenes are either recovered for sale as commercially valuable industrial chemicals or oxidized by the following method and recycled along with the alcohol.

In accordance with Embodiment No. 3 of this invention, a substituted or unsubstituted 2,5-cyclohexadiene-1,4-dione or quinhydrone may be prepared by reacting an aromatic-1,4-dihydroxy compound with oxygen at elevated pressures and at ambient or elevated temperatures in the presence of a copper salt catalyst or a catalyst consisting of metallic ruthenium or rhodium deposited on an inert support, and in solvents comprised of nitrile, alcohol or nitrile-containing solvent mixtures. This regeneration is carried out according to equation 3 of the depiction, supra, wherein $R_1$, $R_2$, $R_3$, and $R_4$ may be hydrogen, aliphatic, aromatic or alicyclic groups or halogens. The halogen may be selected from chlorine, fluorine, bromine or iodine.

The reaction between the 1,4-dihydroxybenzene, oxygen, and metal or metal salt catalyst may be carried out in an autoclave or any other high, medium or low pressure reactor. A general procedure is to charge the reactor with the hydroquinone, the catalyst, the solvent and oxygen at the desired pressure, then to agitate the reaction mixture and to heat, if necessary, for the appropriate period. The reaction may be carried out batchwise or as a continuous process and the order of addition of the reactants varied to suit the particular apparatus employed. The reaction products are then recovered by conventional methods such as distillation, recrystallization, extraction and sublimation, or recycled along with the solvent for use in Embodiments 1 and 2 of this invention.

The solvents which may be used in the performance of Embodiment No. 3 of this invention are the aliphatic, alicyclic or aromatic nitriles, the monohydric saturated aliphatic and alicyclic alcohols, and mixtures of the above-mentioned nitriles and alcohols in any proportion. The alcohols and nitriles may contain other substituents such as halo, alkoxy, carboxy groups, etc., in addition to the hydroxy or nitrile group.

The alcohols, which may be primary, secondary, or tertiary, conform to the general formula ROH wherein R is an optionally substituted aliphatic or alicyclic group preferably containing 1 to 10 carbon atoms. Representative alcohols especially suitable for use in this invention are monohydric alcohols such as methyl, ethyl, n-, iso-, sec-, and tert-butyl, amyl, hexyl, octyl, lauryl, n- and sec-propyl alcohols as well as cyclohexanols, cyclooctanols, cycloheptanols, cyclodecanols, and the like.

The nitriles which may be used in Embodiment No. 3 of this invention may be primary, secondary, or tertiary nitriles conforming to the general formula RCN, wherein R is an optionally substituted aliphatic, aromatic or alicyclic group preferably containing 1 to 10 carbon atoms. Representative nitriles especially suitable for use in this invention are the mono-nitriles such as aceto, acrylo, n- or isobutyro, propio-, valero-, caprio-, caprylio-, or capronitrile as well as benzo-, cyclohexyl-, cyclopentyl-, cycloheptyl- and cyclooctylnitrile.

The 1,4-dihydroxybenzenes which may be regenerated to the 2,5-cyclohexadiene-1,4-dione or quinhydrones in this manner are the mono-, di-, tri-, and tetra-substituted chloro, bromo, fluoro, and iodo compounds, as well as the aliphatic, alicyclic, and aromatic 1,4-dihydroxybenzenes including the mono-, di-, tri-, and tetra-substituted methyl, ethyl, propyl, and isopropyl compounds as well as naphthoquinones and other multi-ring compounds having the 1,4-dihydroxybenzene ring as part of its structure.

In addition to 1,4-dihydroxybenzene itself, representative substituted compounds include, for example, 2-chloro-, 2-bromo-, 2-fluoro-, and 2-iodo-1,4-dihydroxybenzene, 2,5-, 2,6-, and 2,3-dichloro-, dibromo-, difluoro- and diiodo-1,4-dihydroxybenzene, benzene-1,4-diol, 2,3,5-trichloro-, trifluoro-, tribromo-, and triiodo-1,4-dihydroxybenzene and the tetrachloro- (chloranil), tetrabromo (bromanil)-, tetrafluoro- and tetraiodo-1,4-dihydroxybenzene. Representative alkyl substituted 1,4-dihydroxybenzenes are 2-methyl-, 2-ethyl-, and 2-propyl-1,4-dihydroxybenzene, 2,5-, 2,6-, and 2,3-dimethyl-, and diethyl- and dipropyl-1,4-dihydroxybenzene, 2,3,5-trimethyl-, triethyl-, and tripropyl-1,4-dihydroxybenzene, and the 2,3,5,6-tetramethyl- and tetraethyl-1,4-dihydroxybenzene. In addition, such other 1,4-dihydroxybenzenes may also be employed as 2,3-dichloro-5,6-dicyano-1,4-dihydroxybenzene or tetracyano-1,4-dihydroxybenzene.

The metal salt catalysts which may be employed in the process of Embodiment No. 3 of this invention are the copper (I) and copper (II) salts, either alone or a mixture thereof, as well as ruthenium or rhodium metal.

The catalysts employed may be in a homogeneous or heterogeneous state in the reaction mixture. Thus, they may be present in solution, suspended, or they may be deposited on an inert support such as alumina, silica gel, activated carbon or zeolites (*Catalysis*, C. Kemball, ed., Chapter 3, "Catalysis on Faujasitic Zeolites," R. Rudham and A. Stockwell, The Chemical Society, Burlington House, London, pages 87–135, 1977).

The following examples are provided to illustrate the invention in accordance with the previously described embodiments, but are not to be construed as limiting the invention in any way except as indicated by the appended chaims.

Demonstrating Embodiment No. 1 of this invention as shown in the examples which follow, a 2-L Teflon coated stainless steel (Magnedrive) stirred autoclave with Hastelloy C thermowell, stirrer, cooling coils, and sampling tube was employed for the oxidative carbonylation. The reaction products were isolated and analyzed by NMR, FT-IR, X-ray diffraction, and elemental analysis. All yields reflect the yields of isolated, purified product.

EXAMPLE I

To a 2-L autoclave was added 0.99 g (0.0056 m) palladium (II) chloride, 39.9 g (0.3694 m) 2,5-cyclohexadiene-1,4-dione (quinone), and 500 mL absolute methanol. The reactor was sealed, purged with 800 psig nitrogen and 300 psig carbon monoxide, and pressurized to 1500 psig with carbon monoxide while stirring. Heating was begun and continued until the pressure drop ceased. After rapid cooling, the gases were sampled for $CO_2$ and vented. The contents of the reactor were filtered to recover the catalyst. Excess solvent was removed by distillation and the hydroquinone recovered by precipitation from benzene or chloroform. The dimethyl oxalate was recovered by distillation to give 24.87 g or 57.1 percent yield based on the amount of 2,5-cyclohexadiene-1,4-dione charged.

EXAMPLES II–IV

In examples II to IV, the reaction was carried out as in example I except that 0.50 g (0.0028 m) palladium (II) chloride was used as catalyst. Also in examples III and IV, starting pressures of 1450 and 1410 psig, respectively, were employed. The results can be found in table I, infra.

EXAMPLES V–VII

In examples V to VII, the reaction was also carried out as in example I except that a co-solvent was used. The liquid phase consisted of 250 mL absolute methanol and 250 mL dry acetonitrile. The starting pressures for examples V, VI, or VII were 1410, 1430, and 1430, respectively. The results of these examples can also be found in table I, infra.

EXAMPLES VIII–XI

In examples VIII to XI, a metal oxidant salt, copper (II) chloride, was charged to the reactor in addition to the palladium (II) chloride. The starting pressures for the reaction were 1600, 1610, 1615, and 1650 psig, respectively. The reactions were carried out in a similar manner as in example I. The results of these examples may be found in table I, infra.

TABLE I

| Example No. | Catalyst, g | Quinone g | Solvent mL | CO Pressure[a], psig | Total Pressure Drop, psi | Max. Temp., °C. | Run Time, hrs. | Yield of Oxalate g | Yield of Oxalate % | Recovered Hydroquinone % |
|---|---|---|---|---|---|---|---|---|---|---|
| I | PdCl$_2$ (0.99) | 39.9 | CH$_3$OH (500) | 1950 | 170 | 131 | 1.5 | 24.87 | 57.1 | 85.4 |

TABLE I-continued

| Example No. | Catalyst, g | Quinone g | Solvent mL | CO Pressure[a], psig | Total Pressure Drop, psi | Max. Temp., °C. | Run Time, hrs. | Yield of Oxalate g | Yield of Oxalate % | Recovered Hydroquinone % |
| --- | --- | --- | --- | --- | --- | --- | --- | --- | --- | --- |
| II | PdCl$_2$ (0.50) | 39.9 | CH$_3$OH (500) | 1845 | 200 | 124 | 1.5 | 25.83 | 59.3 | 100 |
| III | PdCl$_2$ (0.50) | 39.9 | CH$_3$OH (500) | 1800 | 170 | 121 | 0.8 | 26.96 | 61.8 | 98.4 |
| IV | PdCl$_2$ (0.50) | 39.9 | CH$_3$OH (500) | 1765 | 160 | 115 | 0.6 | 27.58 | 63.3 | 97.1 |
| V | PdCl$_2$ (0.50) | 39.9 | CH$_3$OH (250) CH$_3$CN (250) | 1840 | 180 | 135 | 0.8 | 30.65 | 70.3 | 93.4 |
| VI | PdCl$_2$ (0.50) | 39.9 | CH$_3$OH (250) CH$_3$CN (250) | 1845 | 170 | 138 | 0.8 | 29.00 | 66.5 | 92.1 |
| VII | PdCl$_2$ (0.50) | 39.9 | CH$_3$OH (250) CH$_3$CN (250) | 1845 | 150 | 138 | 0.8 | 29.97 | 68.8 | 95.0 |
| VIII | PdCl$_2$ (0.198) CuCl$_2$ (0.758) | 39.9 | CH$_3$OH (500) | 1990 | 120 | 127 | 2.3 | 21.00 | 48.2 | 97.7 |
| IX | PdCl$_2$ (0.198) CuCl$_2$ (0.758) | 39.9 | CH$_3$OH (500) | 2065 | 190 | 128 | 1.5 | 24.00 | 55.1 | 97.7 |
| X | PdCl$_2$ (0.198) CuCl$_2$ (0.758) | 39.9 | CH$_3$OH (500) | 2100 | 175 | 132 | 1.75 | 25.00 | 57.3 | 85.6 |
| XI | PdCl$_2$ (0.198) CuCl$_2$ (0.758) | 80 | CH$_3$OH (500) | 2030 | 190 | 128 | 1.75 | 40.00 | 45.8 | 89.6 |

[a]Reflects maximum pressure attained during reaction.

EXAMPLES XII–XIV

Several examples were run using solely the copper (II) and copper (I) chloride catalysts as claimed by Zehner. In these cases, the carbon monoxide pressure decreased very slowly with time. A tarry material was obtained from which only small amounts of p-hydroxyphenetole or p-hydroxyanisole could be isolated. The reaction conditions are given in table II below.

0°–5° C. for 30 minutes. The resulting precipitate was filtered to give 26.77 g oxamide (82.3 percent yield based on the oxidant).

EXAMPLES XVI–XVIII

In these runs, 0.50 g (0.0028 m) palladium (II) chloride, 39.9 g (0.3694 m) 2,5-cyclohexadiene-1,4-dione and 500 mL absolute methanol was charged to a 2-L autoclave. The reactor was sealed, purged with nitrogen

TABLE II

Comparative Examples

| Ex. No. | Catalyst (g) | Quinone (g) | Solvent (mL) | CO Pressure[a], psig | Total Pressure Drop, psi | Max. Temp., °C. | Run Time, hrs. | Yield of Oxalate (g) | Yield of Oxalate (%) | Recovered Hydroquinone (%) |
| --- | --- | --- | --- | --- | --- | --- | --- | --- | --- | --- |
| XII | CuCl$_2$ (0.758) | 39.9 | CH$_3$OH (500) | 2110 | 40 | 131 | 7 | 0 | 0 | 0[b] |
| XIII | CuCl$_2$ (1.39) | 39.9 | C$_2$H$_5$OH (350) | 1550 | 100 | 135 | 24 | 0 | 0 | 0[b] |
| XIV | CuCl$_2$ (0.273) | 39.9 | C$_2$H$_5$OH (350) | 1530 | 50 | 133 | 12 | 0 | 0 | 0[b] |

[a]Reflects maximum pressure attained during reaction.
[b]Only a tarry polymeric was obtained, from which some p-phenetole could be distilled.

Examples demonstrating Embodiment No. 2 of this invention follows.

EXAMPLE XV

To a 2-L autoclave was charged 0.50 g (0.0028 m) palladium (II) chloride, 39.9 g (0.3694 m) 2,5-cyclohexadiene-1,4-dione (quinone), and 500 mL absolute methanol. The reactor was sealed, purged with 500 psig nitrogen and 500 psig carbon monoxide, and pressurized to 1400 psig carbon monoxide while stirring at 23° C. Heating was begun, and the reaction was maintained at 130° C. until the pressure drop ceased. The reaction was terminated by rapid cooling and the gases sampled for CO$_2$ formation with none being detected. The reactor was vented and purged with nitrogen. The liquid contents were removed and the catalyst filtered. The filtrate was then ammoniated by bubbling ammonia into the solution under nitrogen and with rapid stirring at and carbon monoxide, and pressurized to 1400–1420 psig with stirring at 23° C. Heating was begun and the reaction temperature maintained at 129°–132° C. until the pressure drop ceased. The reaction was terminated by rapid cooling and the gases sampled for CO$_2$ formation with none being detected. The reactor was vented and purged with nitrogen. The liquid contents were removed and the catalyst filtered. The filtrate was then ammoniated by bubbling ammonia into the solution under nitrogen at atmospheric pressure and at 0°–5° C. with rapid stirring for 30 minutes. The oxamide was filtered and washed. The 1,4-dihydroxybenzene was recovered by removal of the solvent and recrystallization from benzene. The results are given in table III, infra.

EXAMPLE XIX

Example XIX was run as in examples XVI–XVIII except that the liquid phase consisted of 300 mL absolute methanol and 200 mL acetonitrile, and only 0.25 g (0.0014 m) palladium (II) chloride was employed. The starting pressure was 1500 psig at 25.5° C. See table III, infra, for results.

EXAMPLES XX–XXI

Examples XX and XXI were run as in examples XVI–XVIII except that 1 mole (108 g) of 2,5-cyclohexadiene-1,4-dione and 1000 mL absolute methanol were charged to the autoclave in example XX while for example XXI, 0.738 mole (79.8 g) of 2,5-cyclohexadiene-1,4-dione and 750 mL absolute methanol were charged to the autoclave. Starting pressures of 1450 psig and 1610 psig, respectively, were employed. The results are shown in table III, infra.

EXAMPLE XXII

Example XXII was run as in examples XVI–XVII except that the liquid phase consisted of 250 mL absolute methanol and 250 mL dry acetonitrile. A starting pressure of 1520 psig at 25° C. was utilized. See table III, infra, for results.

EXAMPLE XXIII

Example XXIII was run as in examples XVI–XVIII except that 450 mL of methanol was used. Starting pressure was 1520 psig at 25.5° C. See table III for results.

In the runs which follow, quinone was regenerated from hydroquinone (Embodiment No. 3). Except where otherwise stated, a 2-L Parr stirred reactor was employed and the reaction products were isolated by evaporation of the solvent and extraction of the solid residue with n-hexane. The hexane was then evaporated to give pure quinone product.

EXAMPLE XXIV

To a 2-L Parr stirred reactor was charged 10.45-g copper (II) acetate, 55-g hydroquinone, 400-mL acetonitrile and 100-mL water. The reactor was pressurized with oxygen to 125 psig and stirred at ambient temperature for one hour. The reactor was vented, the solvent evaporated, and the residue extracted continuously with hexane via a soxlet extractor. The hexane was then evaporated to give 29.67 g quinone (55 percent yield).

EXAMPLES XXV AND XXVI

To a 2-L Parr stirred reactor was charged 4.94-g copper (I) chloride, 55-g hydroquinone, and 500-mL acetonitrile. The reactor was pressurized with oxygen to 125 psig and stirred for nine hours at ambient temperature. The reactor was vented, the solvent evaporated, and the residue extracted with hexane via a soxlet extractor. The hexane was evaporated to give 49.31 g (91.3 percent yield) quinone. In example XXVI, the oxygen pressure was increased to a value of 200 psig at ambient temperature. After 3.5 hours, workup of the reaction mixture afforded 49.33 g (91.4 percent yield) quinone.

EXAMPLES XXVII AND XXVIII

A 2-L Parr stirred reactor was charged with 10.45-g copper (II) acetate, 55-g hydroquinone, and 500-mL acetonitrile. The reactor was pressurized with oxygen to 125 psig and stirred for 1.5 hours at ambient temperature. The reactor was vented, the solvent evaporated, and the residue extracted with hexane via a soxlet extractor to give 40.08 g (94 percent) quinone. The reaction was repeated and 40.36 g (95 percent yield) quinone was obtained.

TABLE III

| Example No. | $PdCl_2$, g | Quinone g | Methanol mL | CO Pressure[a], psig | Total Pressure Drop, psi | Max. Temp., °C. | Reaction Time, hrs. | Yield of Oxamide g | % | Hydroquinone Recovered % |
|---|---|---|---|---|---|---|---|---|---|---|
| XV | 0.50 | 39.9 | 500 | 1740 | 150 | 130 | 0.6 | 26.77 | 82.3 | —[d] |
| XVI | 0.50 | 39.9 | 500 | 1760 | 180 | 129.5 | 0.55 | 24.57 | 75.6 | 100 |
| XVII | 0.50 | 39.9 | 500 | 1780 | 160 | 132 | 0.6 | 20.69 | 63.6 | 100 |
| XVIII | 0.50 | 39.9 | 500 | 1765 | 170 | 129.5 | 0.6 | 19.92 | 61.3 | 94.6 |
| XIX | 0.25 | 39.9 | 300[b] | 1955 | 120 | 135 | 0.7 | 24.23 | 74.5 | 94.0 |
| XX | 0.50 | 108 | 1000 | 1750 | 580 | 138 | 0.8 | 59.75 | 67.9 | 90.0 |
| XXI | 0.50 | 79.8 | 750 | 1920 | 380 | 143 | 0.6 | 47.42 | 72.9 | 94.0 |
| XXII | 0.50 | 39.9 | 250[c] | 1970 | 170 | 138 | 0.6 | 22.61 | 69.5 | 98.6 |
| XXIII | 0.50 | 39.9 | 450 | 1940 | 150 | 132 | 0.6 | 21.40 | 65.8 | 92.2 |

[a]Maximum pressure achieved during reaction.
[b]200 mL CH₃CN added.
[c]250 mL CH₃CN added.
[d]Hydroquinone recovery was not attempted.

EXAMPLE XXIX

A 2-L Parr stirred reactor was charged with 1.25-g copper (II) chloride, 13.75-g hydroquinone, 230-mL 2-propanol, and 230-mL acetonitrile. The reactor was pressurized with oxygen to 125 psig and stirred at ambient temperature for 29 hours. The reactor was vented, the solvent evaporated, and the residue extracted with hexane via a soxlet extractor. The hexane was then evaporated yielding 12.30 g (91 percent yield) quinone.

EXAMPLE XXX

To a 2-L Parr stirred reactor was charged 2.61 g of copper (II) acetate, 13.75 g of hydroquinone, 230 mL of 2-propanol and 230-mL acetonitrile. The reactor was pressurized with oxygen to 125 psig and stirred at ambient temperature for 16 hours. Workup in the usual manner provided 11.23 g (83 percent yield) quinone.

EXAMPLE XXXI

A 2-L Parr stirred reactor was charged with 1.79 g of copper (II) bromide, 13.75 g of hydroquinone, and 500-mL acetonitrile. The reactor was pressurized with oxygen to 125 psig and stirred at ambient temperature for 29 hours. The reactor was vented and the products worked up as in the previous examples to give 12.30 g (91 percent yield) quinone.

In examples XXIV to XXXI, the yields reported reflect quinone isolated as a solid. Yields of quinone in the reaction mixture approach quantitative conversion, as no solid products other than the quinone and catalyst were recovered. Note that in comparative example XXXII, infra, (and example I) the isolated yields of quinone were much lower when acetic acid (water) was used as a solvent due to its high boiling point, and hence the partial loss of quinone by evaporation.

EXAMPLES XLV–L

A series of experiments was run in which quinhydrone, a one-to-one complex of quinone and hydroquinone, was obtained as the only product. These experiments were conducted with catalyst consisting of rhodium or ruthenium metal deposited on an inert support. The solvent and hydroquinone were charged to the reactor, which was then pressurized with oxygen. The reaction was terminated and the workup provided quinhydrone. The results of these experiments are given in table V below.

TABLE V

Oxidation of Hydroquinone to Quinone With Oxygen at Elevated Pressure

| Example No. | Catalyst, g | Solvent, mL | Hydroquinone charged, g | Oxygen pressure, psig | Temp., °C. | Time, h | Quinhydrone Grams | Percent Conversion |
|---|---|---|---|---|---|---|---|---|
| XLV | 5% Ru/Al$_2$O$_3$ (5.0) | 2-C$_3$H$_7$OH (500) | 13.75 | 125 | 25 | 16 | 13.00 | 95.4 |
| XLVI | 5% Rh/Al$_2$O$_3$ (5.0) | CH$_3$CN (500) | 13.75 | 125 | 25 | 20 | 13.00 | 95.4 |
| XLVII | 5% Ru/C (4.0) | CH$_3$CN (500) | 13.75 | 125 | 25 | 24 | 11.00 | 80.7 |
| XLVIII | 5% Ru/C (4.0) | CH$_3$CO$_2$H (500) | 55 | 125 | 80–5 | 6$^a$ | 44.60 | 81.8 |
| XLIX | 5% Ru/C (4.0) | CH$_3$CO$_2$H (500) | 55 | 125 | 80–5 | 6 | 37 | 67.8 |
| L | 5% Ru/C (4.0) | CH$_3$CN/2-C$_3$H$_7$OH (250/250) | 13.75 | 125 | 25 | 22 | 12.3 | 90.3 |

$^a$The temperature was maintained at 80–5° C. for six hours, after which time the reactor was allowed to stir overnight at room temperature.

EXAMPLE XXXII

A 2-L Parr stirred reactor was charged with 5 g of commercial (5 percent) rhodium supported on alumina, 13.75 g of hydroquinone, and 400-mL acetic acid. The reactor was pressurized with oxygen to 125 psig and stirred for four hours at a temperature of 80°–85° C. The reactor was cooled, vented, and the solvent evaporated. The residue was extracted with hexane via a soxlet extractor. The hexane was evaporated affording 8 g (58 percent yield) quinone.

EXAMPLES XXXIII–XLIV

In these examples, a 150-cc cylinder reactor was charged with the catalyst, 50-mL solvent and 2 g of tetrachlorohydroquinone. The reactor was mechanically shaken until the required pressure drop was acquired. The contents were then filtered and the tetrachloroquinone recrystallized from benzene. The results of these examples (XXXIII–XLIV) are given in table IV below. Although the percent conversion was low in some cases, the amount of starting material recovered indicated the reaction could be carried out with higher conversions under more efficient agitation conditions.

After an examination of the data presented in the examples, supra, and other data which we have assembled in discovering and developing the present invention, we have determined that the operable parameters of the embodiments of our invention are as follows:

The molar ratio of quinone to platinum group metal salt catalyst must be maintained in the range of 3160:1 to 100:1, with the preferred range being between 2000:1 and 100:1. The most preferred range for the ratio of quinone to platinum group metal salt catalyst is between 1000:1 and 316:1. In this range, the reaction proceeds smoothly at a rapid rate, thus lowering the reaction time.

The molar ratio of quinone to metal oxidant salt, if used, must be maintained in the range of 300:1 to 10:1 so as to be effective with the preferred range being between 200:1 and 10:1. The most preferred range for the ratio of quinone to metal oxidant salt is between 100:1 and 10:1.

The molar ratio of alcohol to quinone must be maintained in the range of 100:1 and 3:1, with the preferred range being between 50:1 to 10:1. The most preferred

TABLE IV

Oxidation of Tetrachlorohydroquinone With Oxygen at Elevated Pressures

| Example No. | Catalyst, g | Solvent, mL | TCHQ$^a$ charged, g | Oxygen pressure, psig | Temp., °C. | Time, h | Yield of TCQ$^b$ Grams | Percent Conversion |
|---|---|---|---|---|---|---|---|---|
| Oxidations Utilizing a Mechanically Shaken Reactor | | | | | | | | |
| XXXIII | CuCl (0.08) | 2-C$_3$H$_7$OH (50) | 2.0 | 125 | 25 | 22 | 1.27 | 64 |
| XXXIV | CuSO$_4$ (0.126) | 2-C$_3$H$_7$OH (50) | 2.0 | 125 | 25 | 22 | 0.68 | 32 |
| XXXV | Cu(CH$_3$CO$_2$)$_2$ (0.16) | 2-C$_3$H$_7$OH (50) | 2.0 | 125 | 25 | 20 | 1.58 | 79 |
| XXXVI | 5% Rh/Al$_2$O$_3$ (1.64) | 2-C$_3$H$_7$OH (50) | 2.0 | 125 | 25 | 24 | 1.66 | 83 |
| XXXVII | 5% Ru/C (1.64) | 2-C$_3$H$_7$OH (50) | 2.0 | 125 | 25 | 24 | 1.90 | 95 |
| XXXVIII | CuCl (0.08) | CH$_3$CN (50) | 2.0 | 125 | 25 | 23 | 1.83 | 91 |
| XXXIX | CuSO$_4$ (0.126) | CH$_3$CN (50) | 2.0 | 125 | 25 | 23 | 0.95 | 46 |
| XL | Cu(CH$_3$CO$_2$)$_2$ (0.16) | CH$_3$CN (50) | 2.0 | 125 | 25 | 23 | 0.90 | 45 |
| XLI | 5% Rh/Al$_2$O$_3$ (1.64) | CH$_3$CN (50) | 2.0 | 125 | 25 | 23 | 1.30 | 65 |
| XLII | 5% Ru/C (1.64) | CH$_3$CN (50) | 2.0 | 125 | 25 | 24 | 1.62 | 81 |
| XLIII | CuBr (0.115) | CH$_3$CN (50) | 2.0 | 125 | 25 | 25 | 1.00 | 50 |
| XLIV | CuI (0.52) | CH$_3$CN (50) | 2.0 | 125 | 25 | 25 | 1.10 | 60 |

$^a$TCHQ = tetrachlorohydroquinone.
$^b$TCQ = tetrachloroquinone.

range for the molar ratio of alcohol to quinone is between 25:1 and 10:1.

The temperature should be maintained in the range of 80°–200° C. in order to achieve a high selectivity of oxalate ester over carbonate ester, and for the reaction to proceed at as rapid a rate as possible without ensuing side reactions. The preferred temperature range is between 100° C. and 160° C., while the most preferred temperature range, to minimize the possible side reactions, is between 120° C. and 140° C.

In general, carbon monoxide pressures of between 1000 and 5000 psi ($6.9 \times 10^6$ and $3.45 \times 10^7$ pascals) may be employed, the preferred pressures being between 1200 and 3000 psi ($8.27 \times 10^6$ and $2.07 \times 10^7$ pascals). The most preferred pressure range, from both the standpoint of reaction rate and selectivity and equipment cost, is between 1800 and 2500 psi ($1.2 \times 10^7$ and $1.7 \times 10^7$ pascals). Excess carbon monoxide is generally used to maintain the elevated pressures, and a suitable recycle of the excess carbon monoxide gas may be employed.

The reaction time is generally dependent on the nature of the alcohol being reacted, the presence or absence of solvent as well as its structure, the temperature, the pressure, the amount and type of catalyst and oxidant, as well as on the type of equipment (batch or continuous process) being employed.

After catalyst filtration, the oxalate ester formed during the oxidative carbonylation reaction may be ammoniated in situ under an inert atmosphere. The oxamide thus formed is easily collected by simple filtration. The ammoniation is carried out in a mechanically agitated vessel at relatively low temperatures, preferably between −10° C. and 40° C., with the most preferred temperature range being between 0° C. and 10° C. The ammoniation is carried out with excess ammonia, which facilitates the reaction as a base catalyst. The excess ammonia may be stripped from the filtrate and recycled. The ammoniation is generally carried out at atmospheric pressure, but may also be carried out at elevated ammonia pressures.

Embodiment No. 3 of the present invention relates to the recycle of the 1,4-dihydroxybenzenes formed during the oxidative carbonylation and maintained unreacted in the filtrate after precipitation of the oxamide. The following parameters pertain to the regeneration of the 2,5-cyclohexadiene-1,4-diones from the 1,4-dihydroxybenzenes obtained above.

The reaction can be suitably carried out by contacting oxygen or oxygen-containing gases at the desired pressure with the reaction medium containing solvent, specified reactants and catalysts and heating or cooling to the desired temperature.

In general, oxygen pressures of between 10 and 500 psi ($6.8 \times 10^4$ and $3.4 \times 10^6$ pascals) may be employed. The pressure at which a particular reaction may be run will depend upon the catalyst. The pressure should be maintained, however, preferably between 125 and 200 psi ($8.6 \times 10^5$ and $1.3 \times 10^6$ pascals).

The reaction will proceed at temperatures ranging between 20° C. and 100° C. It is generally preferable to operate the process at temperatures between 20° C. and 80° C. The temperature necessary to effect the reaction will also be dependent upon the catalyst used. Heating or cooling may be employed to maintain the temperature within the desired range.

The catalyst is generally employed as a metal salt or as a supported metal catalyst, in catalytic proportions. Generally, the molar ratio of 1,4-dihydroxybenzene to metal salt catalyst should be between 20:1 and 2:1. The preferred range is between 10:1 and 2:1, with the most preferred range being between 5:1 and 2:1. If the catalyst used is a supported metal catalyst, the molar ratio of 1,4-dihydroxybenzene to metal should be maintained between 300:1 and 10:1, with the most preferred range being between 100:1 and 50:1.

The reaction time is dependent upon the nature of the 1,4-dihydroxybenzene being reacted, temperature, pressure, and on the amount and nature of the catalyst being used as well as upon the solvent and type of equipment being employed.

While we have shown and described particular embodiments of our invention, modifications and variations thereof will occur to those skilled in the art. We wish it to be understood, therefore, that the appended claims are intended to cover such modifications and variations which are within the true scope and spirit of our invention.

What we claim as new and desire to secure by Letters Patent of the United States is:

1. A process for the oxidative carbonylation of substituted or unsubstituted alcohols having between 1 and 10 carbon atoms to produce product oxalate esters eminently suitable for use as fertilizer intermediates and byproduct hydroquinone, which process comprises reacting in a reaction vessel under essentially anhydrous conditions, at pressures in the range between about 1000 psi and about 5000 psi and at temperatures in the range between about 80° C. and about 200° C., a mixture of an alcohol and carbon monoxide or a mixture of an alcohol, carbon monoxide and a co-solvent, said alcohol being either an aromatic alcohol, a monohydric saturated aliphatic alcohol, or a saturated alicyclic alcohol, and said co-solvent being nonreactive to said carbon monoxide under said reaction conditions; said reacting mixture in contact with a platinum group metal salt catalyst, or a complex thereof, and a substituted or unsubstituted quinone, wherein the molar ratio of said quinone:platinum group metal salt ranges between about 3160:1 and about 100:1; subsequently filtering and recycling said catalyst; distilling the resulting reaction product to separate the remaining alcohol or alcohol and co-solvent from said esters; recovering said esters as product; recycling said alcohol or alcohol and solvent to said reaction vessel; and recovering hydroquinone as byproduct.

2. The process of claim 1 wherein said catalyst is selected from the group consisting of platinum (II), palladium (II), rhodium (II), and ruthenium (II) halides, oxalates, acetates or sulfates.

3. The process of claim 1 wherein said oxidative carbonylation is carried out in the presence of a metal oxidant salt whose molar ratio of quinone to metal oxidant salt is between 300:1 and 10:1.

4. The process of claim 3 wherein said metal oxidant salt is selected from the group consisting of copper (II) or copper (I) halide, and mixtures thereof.

5. The process of claim 3 wherein the molar ratio of quinone:metal oxidant salt is in the range between about 200:1 and about 10:1.

6. The process of claim 3 wherein the molar ratio quinone:metal oxidant salt is in the range between about 100:1 and about 10:1.

7. The process of claim 1 wherein said alcohol is selected from the group consisting of methyl, ethyl, isopropyl, n-butyl, and mixtures thereof.

8. The process of claim 1 wherein acetonitrile is utilized in admixture as a co-solvent with said alcohol.

9. The process of claim 1 wherein said quinone is selected from the group consisting of 2,5-cyclohexadiene-1,4-dione, alkyl-, aryl-, halogen-substituted derivatives, and mixtures thereof.

10. The process of claim 9 wherein said halogen-substituted derivatives comprise 2-halo-2,5-cyclohexadiene-1,4-diones, 2,5-, 2,6-, and 2,3-dihalo-2,5-cyclohexadiene-1,4-diones, 2,3,5-trihalo-2,5-cyclohexadiene-1,4-diones and tetrahalo-2,5-cyclohexadiene-1,4-diones.

11. The process of claim 9 wherein said alkyl-substituted derivatives comprise 2-alkyl-2,5-cyclohexadiene-1,4-diones, the 2,5-, 2,6-, and 2,3-alkyl-2,5-cyclohexadiene-1,4-diones, the 2,3,5-trialkyl-2,5-cyclohexadiene-1,4-diones, and tetraalkyl-2,5-cyclohexadiene-1,4-diones.

12. The process of claim 1 wherein said molar ratio quinone:platinum group metal salt is in the range between about 2000:1 and about 100:1.

13. The process of claim 1 wherein said molar ratio quinone:platinum group metal salt is in the range between about 1000:1 and about 316:1.

14. The process of claim 1 wherein said temperature is maintained in the range between about 100° C. and about 160° C.

15. The process of claim 1 wherein said temperature is in the range between about 120° C. and about 140° C.

16. The process of claim 1 wherein said pressure of said carbon monoxide gas is maintained in the range between about 1200 psi and about 3000 psi.

17. The process of claim 1 wherein said carbon monoxide gas pressure is maintained in the range between about 1800 psi and about 2500 psi.

18. The process of claim 1 wherein carbon monoxide gas is recycled to said process.

19. The process of claim 1 wherein said platinum group metal salt is complexed in situ in said reaction vessel with ligands selected from the group consisting of phosphine, phosphite, arsine, stibine, and mixtures thereof.

20. The process of claim 1 wherein a complex of said platinum group metal salt with a ligand selected from the group consisting of phosphine, phosphite, arsine, stibine, and mixtures thereof, is introduced into said reaction vessel.

* * * * *